United States Patent
Roberts

[19]

[11] 3,979,625

[45] Sept. 7, 1976

[54] CERAMIC SPACED SENSOR ASSEMBLY FOR A GAS LEAK DETECTOR

[75] Inventor: John A. Roberts, Lynnfield, Mass.

[73] Assignee: General Electric Company, Schenectady, N.Y.

[22] Filed: June 10, 1975

[21] Appl. No.: 585,643

[52] U.S. Cl. ............................. 313/230; 23/254 E; 29/611; 73/23; 73/27 R
[51] Int. Cl.² ........................................ H01J 27/00
[58] Field of Search .............. 313/230; 73/23, 27 R; 324/33; 338/34; 23/254 E

[56] References Cited
UNITED STATES PATENTS
3,751,968   8/1973   Loh et al. ................................ 73/23

*Primary Examiner*—R. V. Rolinec
*Assistant Examiner*—Darwin R. Hostetter
*Attorney, Agent, or Firm*—Vale P. Myles

[57] ABSTRACT

A sensor assembly for a halogenated gas leak detector is characterized by having a porous ceramic spacer element positioned around a central electrode and around portions of the turns of a helical heater coil in order to hold these component parts and the respective turns of the coil in fixed, spaced-apart relationship. The central electrode and the turns of the heater coil are formed of fine, closely spaced, flexible wire that must be held in a predetermined position when the sensor is assembled. To construct the sensor pursuant to a preferred method of the invention, a coating of porous ceramic material is deposited and cured on the central electrode and the pores of this coating are loaded with an alkali metal salt. The central electrode is then positioned within the heater coil, from which it is insulated by the coating of ceramic material, and a slurry of ceramic cement is applied to completely surround the coated portion of the central electrode and to at least partially surround each of the turns of the heater coil. The slurry is cured to form a ceramic spacer block that serves to position the central electrode and the respective turns of the heater coil in fixed spaced-apart relationship.

9 Claims, 3 Drawing Figures

CERAMIC SPACED SENSOR ASSEMBLY FOR A GAS LEAK DETECTOR

BACKGROUND OF THE INVENTION

This invention relates to sensor assemblies for gas leak detectors, and methods of manufacturing them, and more particularly to sensor assemblies that operate on the positive-ion emission principle and utilize very low levels of sensor wattage; in the range of 500 milliwatts, for example.

In the manufacture of sensor assemblies of the type used in the halogenated gas leak detectors it has been common practice to use various types of "combs" to fill a gap between a central electrode and a surrounding heater anode of the assembly in order to space these components apart. When relatively large diameter wire is used and the heater coils of such sensors are formed to have relatively large outer diameters, a wide variety of conventional spacer combs are suitable for positioning the components in their desired operating relationships. One example of another type of prior art component spacer assembly for a gas leak detector is disclosed in U.S. Pat. No. 3,751,968—Loh, which issued on Aug. 14, 1973. The spacer shown in the Loh patent is a glass-ceramic element having a depletion layer exposed to the atmosphere that is to be sensed. Such prior art spacers are generally suitable for maintaining a desired gap between the central electrode and a surrounding heater coil, however, in devices of the size required for very low level sensor wattages, i.e., in the neighborhood of 500 milliwatts, it has been found that the sensor size must be reduced to such an extent that conventional prior art spacer arrangements such as those shown by Loh are not suitable for maintaining the thin, flexible turns of the heater coil in spaced-apart relationship.

It has also been found to be desirable to provide a convenient means for insulating the central electrode of such a sensor assembly from its surrounding heater anode coil during the assembly of these components prior to the time that a ceramic spacer element is positioned between them to maintain the desired gap. Without such an insulated central electrode, there is some risk that the central electrode may short-circuit the heater coil when it is energized during the manufacturing process.

Accordingly, it is a primary object of the present invention to provide a sensor assembly for a halogenated gas leak detector that is characterized by having a porous ceramic spacer element surrounding its central electrode and at least partially surrounding each of the turns of a heater anode to maintain these component parts in spaced-apart relationship.

Another object of the invention is to provide a sensor assembly for a gas leak detector having a coating of insulating porous ceramic material deposited on a central electrode positioned within the turns of a heater anode coil so that the central electrode cannot be shorted to the coil prior to the time that these components are fixed in spaced-apart relationship by positioning a ceramic spacer element therebetween.

A further object of the invention is to provide an improved method for manufacturing sensor elements for gas leak detectors so that reliable, relatively inexpensive sensor assemblies having a reduced sensor wattage in the range of 500 milliwatts can be consistently manufactured to high quality standards.

Additional objects and advantages of the invention will become apparent to those skilled in the art from the description presented herein when taken in connection with the accompanying drawings.

SUMMARY OF THE INVENTION

In a preferred form of the invention a sensor assembly for a halogenated gas leak detector is formed by depositing a coating of porous ceramic material on a central platinum electrode wire, positioning the central electrode within the turns of a heater anode coil and applying a slurry of ceramic material to the coil and central electrode. The applied slurry is then curred to form a porous ceramic spacer block that tightly surrounds the central electrode and at least partially surrounds each turn of the heater anode coil thereby fixing these component parts of the assembly in position. The heater anode coil is formed of platinum wire having a minimum thickness in the range of 1 to 3 mils and the elongated central electrode is formed of platinum wire having a diameter in the range of ½ to 2 mils. In order to provide alkali metal ions for actuating the sensor assembly, the coating of porous ceramic material deposited on the central electrode is loaded with an alkali metal selected from the class including rubidium carbonate and sodium carbonate before the slurry is applied to encapsulate this coating.

DESCRIPTION OF THE PREFERRED EMBODIMENTS

Figure 1:
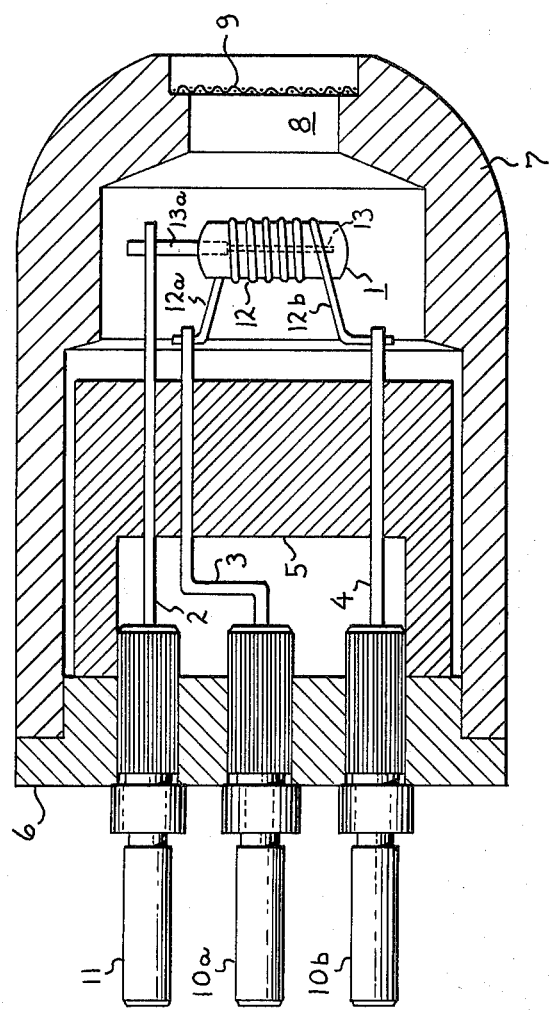
FIG. 1 is a side elevation view, partly in cross-section, illustrating a halogenated gas leak detector having a sensor assembly mounted therein and constructed pursuant to the teaching of the present invention.

Referring now to FIG. 1 of the drawings, it will be seen that there is shown a sensor assembly 1 for a halogenated gas leak detector. The following detailed description of the characteristic features of the sensor assembly will point out its advantages and preferred mode of operation, but first brief reference will be made to one preferred form of relatively conventional housing means that can be used to support the assembly in operating position. The assembly may be housed in any suitable form of commercially available housing; however, in the preferred embodiment of the invention being described the sensor assembly 1 is electrically and mechanically connected to three conductors 2, 3 and 4, which extend through, and are staked to, an insulating spacing member 5. Spacing member 5 is cemented to an insulating base plate 6 which is sealed to a housing cap 7. Gas is permitted to enter the cap 7 through a passageway 8 that is covered with a suitable filter 9 having a sufficiently fine cross-section to prevent contaminating particles from entering the interior of the cap 7.

In order to supply heating current through the conductors 3 and 4, they are connected respectively to a pair of spaced-apart terminals 10 and 10b. Likewise, the conductor 2 is electrically connected to another terminal 11 so that an operating or biasing voltage can be applied across the gap that is formed in the sensor assembly 1 between an electrode connected to conductor 2 and an anode connected to the conductors 3 and 4. It will be appreciated that a wide variety of different conventional structures may be used to form the components of the leak detector sensor assembly housing and terminals described thus far.

The sensor assembly of the present invention is characterized by being formed to operate on a very low sensor wattage, i.e., in the neighborhood of 500 milliwatts. This very low power level requires that the physical dimension of the sensor components be reduced to a point where the helical anode heater coil 12 is formed of platinum wire (or a suitable platinum alloy) having a minimum thickness or diameter in the range of 1 to 3 mils, while the elongated central electrode 13 (also see FIG. 2) positioned within the anode coil 12 to substantially parallel the longitudinal axis thereof is formed of platinum wire having a diameter in the range of ½ mil to 2 mils. The flexible nature of such thin wires presents a number of problems both in the manufacture and field application of such sensor assemblies, as explained more fully above. Moreover, in the relatively small size sensor assembly being described, the outside diameter of the coil 12 is preferably in the range of 0.01 to 0.02 inches (although shown on an enlarged scale in FIGS. 1 and 2 to clarify its illustration). In operation a biasing voltage is applied between the central electrode 13 and the surrounding anode coil 12 by coupling the terminals 10 and 11 and the ground terminal to conventional power sources, as is well known in the gas detector art.

Figure 2:
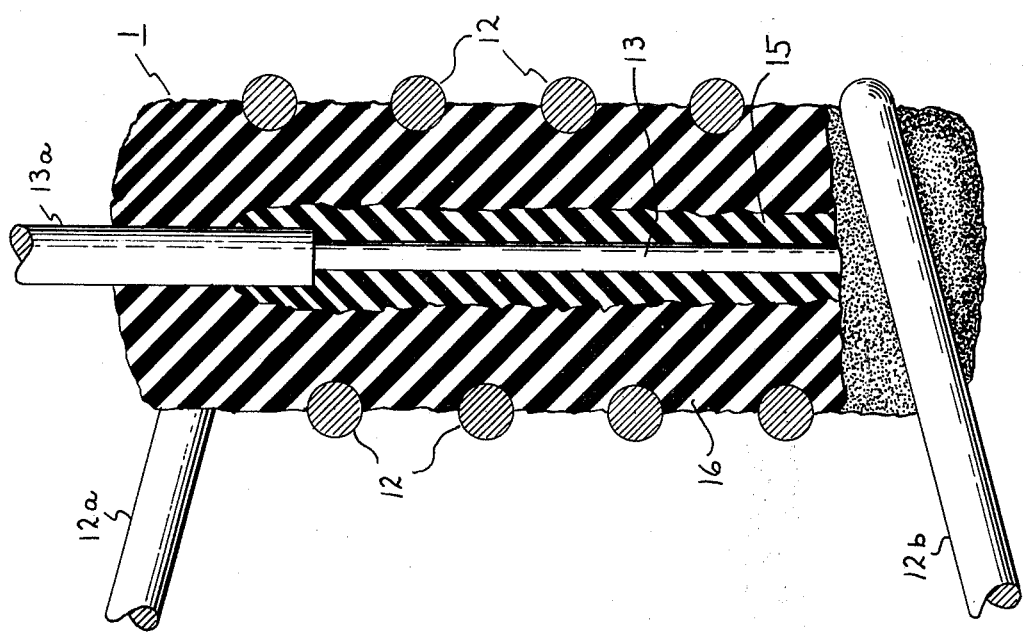
FIG. 2 is an enlarged side elevation view of the sensor assembly for the gas leak detector illustrated in FIG. 1 showing, partly in cross-section, and partly in schematic form, the characteristic features of the sensor assembly.

Turning now to the enlarged drawing of the sensor assembly 1 that is illustrated in FIG. 2, it will be seen that the central electrode 13 actually comprises a relatively thick support portion 13a and an inner extension in the form of the thin platinum wire 13. In the type of sensor assembly being described in the preferred embodiment of the invention, which utilizes a positive ion emission principle, rather than a depletion layer principle, the heater anode coil should be operated at a temperature in the range between 600°C and 1200°C, preferably around 900°C. On the other hand, the central electrode 13 should preferably be maintained at a temperature approximately 40°C lower than that of the anode coil 12. To accomplish this temperature differential, the size of the support wire 13a connected to central electrode 13 may be varied in diameter to control its heat sink characteristics and limit the loss of heat from the central electrode 13. In this embodiment of the invention, the diameter of the support wire 13a is approximately twice the diameter of the selected central electrode 13.

In order to provide the above-stated desired objectives of the invention, pursuant to its teachings, the central electrode 13 is covered with a coating of cured porous ceramic material 15, a portion of the one end of which is shown schematically in cross-section in FIG. 2. In the preferred embodiment of the invention, the ceramic material 15 is a coating of alumina that is electrodeposited by a conventional commercially available electrostatic painting process over the central electrode 13 and the innermost portion of the support wire 13a. The coating of porous ceramic material 15 serves two desirable functions. First, it serves as an insulator to prevent the central electrode 3 from short-circuiting the respective turns of anode coil 12. Second, the pores of the ceramic material 15 provide a desirable structure for holding an alkali metal salt in close proximity to the central electrodes 13. Thus, also selected from a class including rubidium carbonate and sodium carbonate is disposed in the pores of the ceramic material 15. Various methods may be utilized to deposit the alkali metal salt, but in the preferred embodiment of the invention the central electrode 13, coated with the porous ceramic material 15, is dipped in a solution of rubidium carbonate and fired to sinter the rubidium carbonate and secure it in position in the pores of the ceramic material 15.

The remainder of the sensor assembly 1 (illustrated in FIG. 2) comprises a block of cured porous cement 16, a portion of one end of which is shown in cross-section in FIG. 2 to schematically illustrate its porous and insulating features. The block of cement 16 is formed to have several important unique features, pursuant to the present invention. It is formed tightly around the central electrode 13 to completely encapsulate and thus serve as an excellent heat shield for it. The cement block 16 is also formed around at least the innermost 120 arcuate degrees of the surface of each turn of the heater anode coil 12 in order to securely position the respective turns of the coil in fixed relationship in the final assembly. In fact, as shown in FIG. 2, the respective turns of the coil 12 are preferably more completely covered so that at least 180 degrees of their circumference is in heat exchange relationship with the block of cement material 16.

An important feature of the porous cement material used in practicing the invention is that it does not contain an appreciable amount of silica ($SiO_2$), because it has been found that glass loaded cement will erode platinum wires, particularly wires of the extremely fine diameters used in the low sensor wattage type construction of the preferred form of the invention. Various commercially available Alumina cements having low glass content may be used to form the porous cement block 16, but in the preferred embodiment of the invention the block 16 formed of an Alumina composition having substantially the following make-up:

$Al_2O_3$ = 99% by weight,
$SiO_2$ = 0.7% by weight,
$Se_2O_3$ = 0.1% by weight,
$CaO$ = 0.1% by weight, and
$Na_2O$ = 0.3% by weight.

It has been found that if porous ceramics having not more than 1% Silica in their compositions are utilized in practicing the invention, the operating life of the fine platinum electrode and anode of the sensor assembly 1 is not unduly shortened.

Figure 3:
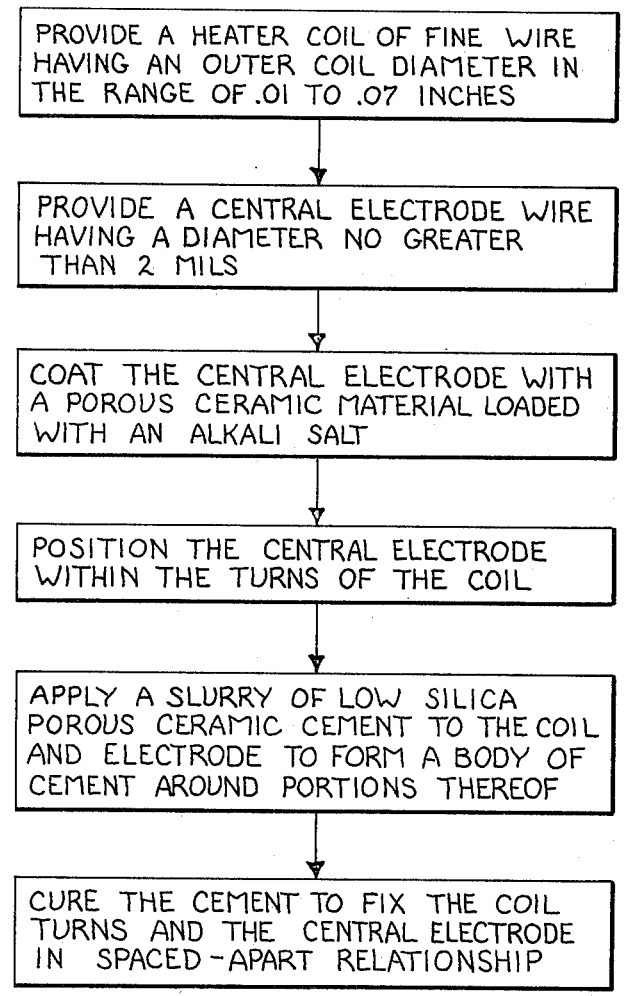
FIG. 3 is a flow chart diagram illustrating the steps of a preferred method for manufacturing a sensor assembly pursuant to the teachings of the invention.

A significant feature of my invention is the novel method utilized to form the block of porous cement material 16 tightly around the central electrode 13 and the turns of anode 12 in order to hold them in the desired spaced-apart relationship. To describe a preferred form of this method of the invention, reference may now be made to FIG. 3 which forms a flow chart of the most preferred method for making the cement block 16. The first four steps outlined in the initial blocks of this flow chart have already essentially been described in explaining the structure of the invention; thus, initially one would provide a heater coil of fine wire having an outer coil diameter in the range of 0.01 to 0.02 inches to form a low sensor wattage assembly of the type described herein. Next, a suitably fine diameter central electrode wire having a diameter no greater than 2 mils would be provided and coated with a porous ceramic material loaded with a suitable alkali salt, as described above. Then, the central electrode would be mechanically positioned within the turns of the heater anode 12, as generally shown in FIG. 2. At that point, pursuant to the method of the invention, a slurry of low Silica porous ceramic cement, such as that described above, would be formed with water and applied to the coil 12 and the central electrode 13, preferably by dipping these components in a bath of the slurry. The components are then removed from the bath and allowed to dry and cure, so that the cement block material 16 thus locks the turns of the coil 12 and the central electrode 13 in their desired spaced-apart relationship. In practicing alternative forms of the invention, it has been found that by applying a voltage of approximately ½ volts to the coil leads 12a and 12b for about 5 seconds, the curing process for the cement material 16 can be enhanced. In particular, if this drying current is sufficient to hold the temperature of the coil 12 in the neighborhood of 1300°C for at least 5 seconds, cement material 16 will be desirably sintered around the coil turns 12 to improve the heat transfer capabilities therebetween.

In practicing the preferred embodiment of the method of the invention, the coating of porous ceramic material deposited on the central electrode 13 is preferably achieved by a commercially available electrostatic painting process, as mentioned above, but it should be noted that the coating is preferably at least 1 mil thick over substantially the entire length of the central electrode 13 in the most preferred embodiment of the invention, in order to afford the above-mentioned desirable insulating properties for the central electrode. Also, in the most preferred embodiment of the invention, the alkali metal salt impregnated in the pores of the coating on central electrode 13 is preferably rubidium carbonate, although sodium carbonate and other suitable alkali salts may be employed in alternative embodiments of the invention.

From the foregoing description of the invention, those skilled in the art will understand that various alterations and modifications of the invention may be made without departing from its true spirit; accordingly, it is my intention to define the limits and encompass the true scope of the invention in the following claims.

What I claim is:

1. A sensor assembly for a halogenated gas leak detector comprising a helical heater coil formed of platinum wire having a thickness in a range of 1 to 3 mils, an elongated electrode positioned within said coil substantially parallel to the longitudinal axis thereof, said electrode being formed of platinum wire having a diameter in the range of 0.5 mil to 2 mils, a coating of cured porous ceramic material deposited on the portion of said electrode disposed within the coil to stiffen and insulate the electrode, an alkali metal salt selected from the class including rubidium carbonate and sodium carbonate being disposed in the pores of said ceramic material, and a block of cured porous cement formed tightly around the coating on said central electrode and around at least the innermost 120 arcuate degrees of the surface of each turn of said coil thereby to position the electrode and coil and the respective turns of the coil in fixed relationship to one another, said coil and electrode being connectable to a source of electric energy for applying a voltage across the gap between the coil and electrode and for supplying heating current to the coil.

2. An invention as defined in claim 1 wherein the outside diameter of said coil is no greater than 0.020 inches.

3. An invention as defined in claim 2 wherein said block of porous cement surrounds at least 180 arcuate degrees of the surface of each coil turn.

4. An invention as defined in claim 3 wherein said cement contains about 99 percent by weight $Al_2O_3$ and not more than 1 percent $SiO_2$.

5. An invention as defined in claim 2 wherein said block of porous cement is formed by applying a slurry of uncured cement to the coil and electrode in their assembled relationship then air drying the cement to cure it in position around the turns of the coil.

6. An invention as defined in claim 5 wherein said block of porous cement is further cured by applying heating current through said coil to raise its temperature to about 1300°C for at least 5 seconds.

7. An invention as defined in claim 6 wherein said coating of porous ceramic material is deposited on the central electrode by an electrostatic painting process.

8. An invention as defined in claim 7 wherein said coating is at least 0.001 inches thick.

9. An invention as defined in claim 8 wherein said coating is dipped in a solution of rubidium carbonate and fired to sinter the material in the pores of the coating.

* * * * *